United States Patent [19]

Pasini

[11] Patent Number: 5,348,474
[45] Date of Patent: Sep. 20, 1994

[54] METHODS OF RECORDING DYNAMICO-FUNCTIONAL DENTAL IMPRESSIONS

[76] Inventor: Giovanni Pasini, via Giuseppe Giusti 2/2, 20059 Vimercate, Italy

[21] Appl. No.: 23,849

[22] Filed: Feb. 26, 1993

Related U.S. Application Data

[60] Continuation-in-part of Ser. No. 764,770, Sep. 24, 1991, abandoned, which is a division of Ser. No. 574,642, Aug. 29, 1990, abandoned, which is a continuation-in-part of Ser. No. 420,365, Oct. 12, 1989, abandoned.

[30] Foreign Application Priority Data

Nov. 4, 1988 [IT] Italy ............................... 22507 A/88

[51] Int. Cl.$^5$ ............................................ A61C 9/00
[52] U.S. Cl. ........................................ 433/214; 523/109; 433/168.1; 433/171; 433/199.1
[58] Field of Search ............. 523/109; 433/214, 168.1, 433/171, 199.1

[56] References Cited

U.S. PATENT DOCUMENTS

| | | | |
|---|---|---|---|
| 2,600,134 | 6/1952 | Sowa et al. | 523/109 |
| 2,628,948 | 2/1953 | Kunze et al. | 524/312 |
| 3,061,572 | 10/1962 | Packer | 524/463 |
| 4,956,404 | 9/1990 | Pelzig | 524/563 |

FOREIGN PATENT DOCUMENTS 1073688 1/1960 Fed. Rep. of Germany.

OTHER PUBLICATIONS

*Hawley's Condensed Chemical Dictionary*, pp. 945, 1170 (11th ed., 1987).
Brown, *Br. Dent. J.*, 164: 357–360 (1988).
Phillips, *Skinner's Science of Dental Materials*, p. 209 (8th ed., 1982).

*Primary Examiner*—Judy M. Reddick
*Attorney, Agent, or Firm*—Kirschstein, Ottinger, Israel & Schiffmiller

[57] ABSTRACT

Methods of recording a muco-dynamic or immediate functional impression of the dental arches of a patient onto the base or peripheral borders of a prosthetic denture, or rebasing a patient's prosthetic denture, utilizing a non-ionic, non-hydrophilic, impression-forming composition comprising polyvinyl acetate, aliphatic ketones, aliphatic esters, aliphatic alcohols or aliphatic ethers, non-toxic, non-aromatic, plasticizing oils and non-toxic and non-extractable organic pigments.

8 Claims, No Drawings

METHODS OF RECORDING DYNAMICO-FUNCTIONAL DENTAL IMPRESSIONS

CROSS-REFERENCE TO RELATED APPLICATIONS

This application is a continuation-in-part of copending Ser. No. 07/764,770, filed Sep. 24, 1991 now abandoned which was a division of Ser. No. 07/574,642, filed Aug. 29, 1990, now abandoned, which was a continuation-in-part of Ser. No. 07/420,365, filed Oct. 12, 1989, now abandoned.

BACKGROUND OF THE INVENTION

The present invention concerns the field of dental mechanics and more particularly the recording of impressions of the dental arches, which constitutes the necessary prerequisite for subsequent construction of a movable prosthesis.

The present invention covers methods utilizing a new composition with which a true mucodynamic impression of the dental arches can be obtained and which exhibits chemical and physical characteristics that are entirely new in comparison with the conventional materials.

The impression of a patient's dental arches is at present recorded with various types of materials. A first group of such materials, well known in the dentistry field, consists, for example, of alginates, irreversible colloids, plaster of Paris, zinc oxide and eugenol paste, silicones, and polyether resins. With these materials, however, the osteomucous complex of the patient's mouth is fixed in a static position (patient motionless with mouth open), and the impression obtained—a so-called "mucostatic" impression, relates to the condition in which the tissues are placed at the precise moment of recording, whereas it is well known that during mastication the soft tissues on which the prosthesis will rest undergo numberless shifts and movements, which cannot be exactly defined with any apparatus, and even less can they be recorded by means of one or more impressions. The proof of this, as all dentists are well aware, can be seen in the fact that if a score of impressions are taken from the same patient with the same material, no two that are identical with each other will be found at the end.

It follows that a dynamic impression is necessary, i.e. an impression with characteristics such as to be faithful to all movements the patient makes in talking, smiling, chewing, etc.

For this purpose the so-called "conditioning" resins, which are in fact only normal acrylic resins containing plasticizers to keep them soft, have been brought onto the market.

If they are applied at the base of the prosthesis and if the patient is made to carry out certain mandibular movements, these resins reproduce the movement of the soft tissues with a certain approximation; after a few minutes, however, as they are thermosetting and not thermoplastic, they no longer change their form. Left in the mouth for a period ranging from a week to several weeks, these resins act on the oral tissues and "condition" them, i.e. modify the position and mobility of the tissues; when this has been achieved, they are removed and replaced by rigid acrylic resin forming part of the prosthesis.

It is thus evident that even in this case the impressions are not mucodynamic, but we have an "adjustment of the tissues to the impression" and for this reason they are known as conditioning resins.

To record a true mucodynamic impression that is the sum or resultant of the multiple tissue variations that take place over time, it is thus necessary to find a material with entirely different functional characteristics, and in particular which can:

(a) be spread on the base of the dental plate and modeled on the dental arches, (b) retain its plasticity for a sufficient period of time to reproduce all those above-mentioned numberless spontaneous movements of the tissues, and (c) harden enough to be subjected to the subsequent processing stages.

SUMMARY OF THE INVENTION

The purpose of the present invention is to provide methods utilizing a new composition to record mucodynamic impressions of dental arches, such that they will meet the aforementioned requirements and at the same time exhibit new and improved chemical and functional characteristics as compared with materials already in use for the purpose, and which are based on acrylic and methacrylic monomers which are made to harden by polymerization in situ (i.e. in the patient's mouth).

This purpose is achieved by means of a new composition according to the present invention, distinguished by the fact of exhibiting the particular features set out in the characterizing part of claim 1. Further developments and specific uses of the composition are set out in the characterizing parts of the succeeding claims.

DETAILED DESCRIPTION OF THE INVENTION

A composition to be utilized in the methods of the present invention consists, for example, of a mixture of polyvinyl acetate, plasticizing oils and non-toxic coloring pigments, in addition to other possible additives of various types, which mixture is rendered plastic and hence suitable for modelling by means of solvents, which are again non-toxic, such for example as low aliphatic alcohols, ketones and esters. In this way:

(a) the composition which is used in the invention is plastic when modelled on the patient's prosthesis and dental arches and retains its plasticity, necessary for recording of the mucodynamic impression, for a long time by virtue of the slow and controlled evaporation of the solvents, (b) the controlled hardening of the composition which is used in the invention, necessary for the subsequent processing stages, takes place, as has been said, through controlled evaporation of the solvents and not by catalyzed polymerization of acrylic and methacrylic monomers in situ, and (c) the composition contains only ingredients compatible with the use made of it, and which are non-toxic and not dangerous, and therefore does not contain, for example, any peroxide-based catalysts and aromatic amine-based inhibitors that would have to be used for the controlled polymerization of acrylic and methacrylic monomers in the mouth, and does not contain any aromatic plasticizing oils or compounds such as cresol derivatives.

The composition which is used in the methods of the present invention comprises the following ingredients in about the concentration ranges indicated:

| Ingredients | Concentration Range | Preferred Range |
| --- | --- | --- |
| Polyvinyl acetate (PVAc) | 50–85% by weight | 65–80% |
| Low ($C_3$ to $C_6$) aliphatic ketones | 2–25% by weight | 5–24% |
| Low ($C_3$ to $C_8$) aliphatic esters | 1–25% by weight | 2–22% |
| Low ($C_2$ to $C_{10}$) aliphatic alcohols and/or aliphatic ethers | 1–25% by weight | 5–24% |
| Non-toxic, non-aromatic, plasticizing oils selected from the group consisting of dioctyl adipate, glycerol triacetate and polyglycols | 0.5–10% by weight | 0.5–5% |
| Non-toxic and non-extractable black, yellow, red or white organic pigments | 0–2% by weight | 0.05–1% | and is free of any gel-forming components, peroxide-based catalysts, aromatic amine-based inhibitors, aromatic plasticizing oils or compounds and incompatible plasticizers.

According to the invention, the low aliphatic ketones and esters are preferably selected from the group comprising acetone, methyl ethyl ketone, ethyl formate, isopropyl and normal propyl formate and acetate, and ethyl acetate.

According to the invention, the low aliphatic alcohols and/or ethers are preferably selected from the group comprising ethyl, isopropyl and normal propyl alcohol, and ethyl and isopropyl ether.

Plasticizing oils other than the compounds specified above may be utilized in the novel composition, provided they are non-aromatic, safe and appropriate for use in the oral environment, have boiling points exceeding 200° C., and are compatible with PVAc. Incompatible plasticizers, i.e., those which are not mutually miscible with PVAc at all relevant temperatures, may not be used in the composition.

The organic pigments mainly considered are red, yellow, black and/or white pigments, alone or in combination, for optimal chromatic preparation in imitation of the oral mucosa coloring.

The aliphatic ketones, esters, alcohols and ethers of low molecular weight which are used as components of the novel composition are selected for their volatility and water-extractability. Once the novel composition is placed in the mouth, these components are gradually extracted by the water in the saliva, leading to progressive but gradual hardening of the PVAc layer. It is also important that these components and the plasticizing oils utilized are non-aromatic, non-toxic and non-carcinogenic.

The novel composition, in order to improve the chemical and functional characteristics described, may also contain additives such as ethylcellulose, methylcellulose and/or cellulose acetate (0–6% by weight), ZnO (0–4% by weight), $TiO_2$ (0–4% by weight), and if required also methacrylate copolymers (copolymers of methacrylic acid esters), PVC, ethylenevinylacetate polymers and/or vinyl chloride and vinyl acetate copolymers (0–10% by weight).

The novel composition is non-ionic and non-hydrophilic, and generally is a high viscosity liquid at ambient temperatures. Although the composition adheres firmly to the base of a prosthesis to which it is applied, it does not adhere to the oral mucosa, and thus permits movement of the prosthesis in relation to the mucosa so that a true mucodynamic impression can be obtained. The composition is substantially free of any gel-forming components.

Moreover, the composition is not significantly viscoelastic and does not "snap back" after deformation, but instead retains the impression of the mucosa during mastication.

Methods of using the above described new composition in accordance with the present invention are as follows:

Recording a Mucodynamic Impression of the Dental Arches

After a denture has been made by conventional methods, the composition forming the subject of the invention is heated to a temperature at which it is plastic and spreadable, usually about 50° C., and spread on the base of the denture which is placed in the patient's mouth. After about 3–4 days, during which the patient will have carried out all the above-mentioned infinite spontaneous movements, which will be recorded and remain impressed on the new composition forming the subject of the invention by virtue of its protracted plasticity, the new composition will, as a result of controlled evaporation of the solvents, be sufficiently hardened to be subjected to the subsequent processing stages (casting of a model in plaster of Paris).

To what has so far been set out in description of the characteristics and practical use of the new composition devised for recording impressions on dental arches and characterized by programmed hardening in the oral cavity (mucodynamic deferred impression), it must be added that the said material can be employed in other useful applications, as described below:

Recording an Immediate Functional Impression

The method described above for recording a mucodynamic impression is followed, but the denture is left in the mouth for only about 10–20 minutes and then removed after rinsing the mouth with very cold water in order temporarily to stop thermo-plasticity of the impression so that a plaster of Paris casting can be made.

Rebasing of Dental Prostheses

Total or partial prostheses that are unstable or damaging to the mucosa may be rebased temporarily with the novel composition by heating the composition to a temperature at which it is plastic and spreadable, applying the composition to the areas of the denture requiring rebasing and inserting the denture into the patient's mouth. Permanent or semipermanent rebasing of restricted prosthetic areas to compensate for bone reabsorption after extraction of teeth, to cushion painful spots, etc., may also be achieved by applying the novel compositions in accordance with the method described above to the areas to be rebased and inserting the denture into the patient's mouth.

Functional Modelling of Peripheral Borders

The novel compositions can be used to create functional impressions of the peripheral borders of old or new unstable dentures to determine the exact form of the peripheral seal required to stop air from entering between the mucosa and the prosthesis. The method described above for applying the composition to the prosthesis can be utilized, but the composition is applied only to the borders of the denture base and an exact functional impression of the "peripheral seal" obtained.

It comes within the framework of the present invention to replace the given individual ingredients of the composition with other compatible ingredients, which can be freely selected by the technician in this field within the framework and in the spirit of the invention illustrated.

The following are illustrative examples of the novel composition used in the methods of the invention, but are not intended to limit the scope of the claimed invention in any way:

| Ingredients | EXAMPLE 1 | EXAMPLE 2 |
|---|---|---|
| | Weight Concentrations (%) | |
| PVAc | 75.00 | 76.00 |
| Glycerol Triacetate | 0.87 | 0.97 |
| Ethyl alcohol | 1.00 | 6.90 |
| Ethyl Acetate | 1.00 | 1.00 |
| Acetone | 22.00 | 15.00 |
| Red Pigment | 0.10 | 0.10 |
| Yellow Pigment | 0.03 | 0.03 |

What is claimed as new and desired to be protected by Letters Patent is set forth in the appended claims.

I Claim:

1. A method of recording a mucodynamic impression of the dental arches of a patient or of the peripheral areas of said arches onto the base or peripheral borders of a prosthetic denture utilizing a non-ionic, non-hydrophilic impression-forming composition comprising:

| | |
|---|---|
| Polyvinyl acetate (PVAc) | 50–85% by weight |
| $C_3$ to $C_6$ aliphatic ketones | 2–25% by weight |
| $C_3$ to $C_8$ aliphatic esters | 1–25% by weight |
| $C_2$ to $C_{10}$ aliphatic alcohols or aliphatic ethers | 1–25% by weight |
| Non-toxic, non-aromatic, plasticizing oils selected from the group consisting of dioctyl adipate, glycerol triacetate and polyglycols | 0.5–10% by weight |
| Non-toxic and non-extractable black, yellow, red or white organic pigments | 0–2% by weight, | and is free of any gel-forming components, peroxide-based catalysts, aromatic amine-based inhibitors, aromatic plasticizing oils or compounds and incompatible plasticizers, said method including the steps of:
 (a) heating said composition to about 50° C. and spreading the heated composition on the base or peripheral borders of the denture;
 (b) inserting the denture into the patient's mouth and allowing it to remain in the mouth for about 3–4 days; and
 (c) removing the denture from the patient's mouth.

2. A method of recording an immediate functional impression of the dental arches of a patient onto the base of a prosthetic denture utilizing a non-ionic, non-hydrophilic impression-forming composition comprising:

| | |
|---|---|
| Polyvinyl acetate (PVAc) | 50–85% by weight |
| $C_3$ to $C_6$ aliphatic ketones | 2–25% by weight |
| $C_3$ to $C_8$ aliphatic esters | 1–25% by weight |
| $C_2$ to $C_{10}$ aliphatic alcohols or aliphatic ethers | 1–25% by weight |
| Non-toxic, non-aromatic, plasticizing oils selected from the group consisting of dioctyl adipate, glycerol triacetate and polyglycols | 0.5–10% by weight |
| Non-toxic and non-extractable black, yellow, red or white organic pigments | 0–2% by weight, | and is free of any gel-forming components, peroxide-based catalysts, aromatic amine-based inhibitors, aromatic plasticizing oils or compounds and incompatible plasticizers, said method including the steps of:
 (a) heating said composition to about 50° C. and spreading the heated composition on the base or peripheral borders of the denture;
 (b) inserting the denture into the patient's mouth and allowing it to remain in the mouth for about 10–20 minutes;
 (c) rinsing the mouth with water;
 (d) removing the denture from the patient's mouth.

3. A method of rebasing a patient's prosthetic denture on a temporary, semipermanent or permanent basis utilizing a nonionic, non-hydrophilic impression-forming composition comprising:

| | |
|---|---|
| Polyvinyl acetate (PVAc) | 50–85% by weight |
| $C_3$ to $C_6$ aliphatic ketones | 2–25% by weight |
| $C_3$ to $C_8$ aliphatic esters | 1–25% by weight |
| $C_2$ to $C_{10}$ aliphatic alcohols or aliphatic ethers | 1–25% by weight |
| Non-toxic, non-aromatic, plasticizing oils selected from the group consisting of dioctyl adipate, glycerol triacetate and polyglycols | 0.5–10% by weight |
| Non-toxic and non-extractable black, yellow, red or white organic pigments | 0–2% by weight, | and is free of any gel-forming components, peroxide-based catalysts, aromatic amine-based inhibitors, aromatic plasticizing oils or compounds and incompatible plasticizers, said method including the steps of:
 (a) heating said composition to about 50° C.
 (b) applying said heated composition to the areas of the denture requiring rebasing; and
 (c) inserting the denture into the patient's mouth.

4. A method according to claims 1, 2 or 3 wherein said aliphatic ketone is acetone.

5. A method according to claims 1, 2 or 3 wherein said aliphatic ester is ethyl acetate.

6. A method according to claims 1, 2 or 3 wherein said aliphatic alcohol is ethyl alcohol.

7. A method according to claims 1, 2 or 3 wherein said plasticizing oil is glycerol triacetate.

8. A method according to claims 1, 2 or 3 wherein said pigments are red or yellow pigments.

* * * * *